United States Patent [19]

Koizumi et al.

[11] Patent Number: 5,113,137
[45] Date of Patent: May 12, 1992

[54] METHOD AND APPARATUS FOR REDUCING IMAGE NOISES

[75] Inventors: Hideaki Koizumi, Katsuta; Koichi Sano, Sagamihara; Tetsuo Yokoyama, Tokyo; Kazuya Sukegawa, Ibaraki, all of Japan

[73] Assignee: Hitachi, Ltd., Tokyo, Japan

[21] Appl. No.: 579,581

[22] Filed: Sep. 10, 1990

[30] Foreign Application Priority Data

Sep. 12, 1989 [JP] Japan .................................. 1-236515

[51] Int. Cl.⁵ .......................................... G01R 33/20
[52] U.S. Cl. ...................................... 324/307; 382/52; 324/309
[58] Field of Search ..................... 382/52; 356/71; 340/705; 250/332; 324/300, 307, 309, 308

[56] References Cited

U.S. PATENT DOCUMENTS

| | | | |
|---|---|---|---|
| 3,915,548 | 10/1975 | Opittek et al. | 340/705 |
| 4,792,226 | 12/1988 | Fishbine et al. | 356/71 |
| 4,811,414 | 3/1989 | Fishbine et al. | 382/52 |
| 4,873,398 | 10/1989 | Hubby, Jr. | 340/705 |
| 4,982,092 | 1/1991 | Jehle | 250/332 |

*Primary Examiner*—Michael J. Tokar
*Attorney, Agent, or Firm*—Antonelli, Terry, Stout & Kraus

[57] ABSTRACT

There is provided an image noise reduction method for improving the signal-to-noise ratio of an image when observed. The image signal of an identical region is measured twice at different times. Images obtained by respective measurements and seen from an identical visual point are so juxtaposed on an identical plane as to form two sheets. By seeing the two sheets of images with parallax changed directly or through stereo glass, the effective signal components of the images are focused on the same plane whereas only noise components are dispersed in a direction perpendicular to the plane.

5 Claims, 4 Drawing Sheets

METHOD AND APPARATUS FOR REDUCING IMAGE NOISES

BACKGROUND OF THE INVENTION

The present invention relates to an image noise reduction method and apparatus for causing three-dimensional dispersion of noise components of images in the visual space to remove noises from images.

In conventional MRI apparatuses for making a diagnosis on a patient by using nuclear magnetic resonance phenomena, noises are removed from images obtained as a result of diagnosis typically by passing image signals through an analog or digital filter and removing noises from images in that filter.

When the noise removing method using a filter such as the above described prior art is used, however, it is difficult to completely remove image noises and the signal-to-noise ratio of images is lowered. Therefore, there is a limit in obtaining clear images. On the other hand, MRI apparatuses are requested to provide clear images in order to improve the accuracy of diagnosis.

It is well known to obtain a stereoscopic image by juxtaposing on the same plane two sheets of images reconstructed with changed visual points from image data which are measured three-dimensionally by the 3DFT method and observing these images with left and right eyes as described in JP-A-63-290548, for example.

This method is shown in FIG. 1. With respect to an image 43 containing three-dimensional information obtained by using the 3DFT method, respective points of image information seen from each of eyes 41 and 42 are added together to obtain two sheets of images seen from respective visual points. The two sheets of images are juxtaposed on an identical plane and are observed with both eyes brought near the center or through stereo glass. A region to be observed is thus obtained as a stereoscopic image.

SUMMARY OF THE INVENTION

An object of the present invention is to provide a image noise reduction method and apparatus capable of improving the signal-to-noise ratio of images and providing clear images.

The image noise removing method of the present invention is a completely novel one we have never had. The image noise reduction method of the present invention comprises the steps of taking a plurality of sheets of images of an identical region from an identical visual point at different times, displaying two sheets of images taken at different times and included in those plurality of sheets of images taken on an identical plane side by side, observing two sheets of displayed images directly or through stereo glass by using both left and right eyes with parallax changed, and thereby three-dimensionally dispersing noise components of images in a direction perpendicular to the image face to remove noises from images.

If the image of an identical region is taken from an identical visual point at different times to produce a plurality of sheets of images, images respectively having different noise components can be obtained. If these images are simultaneously displayed on an identical plane and observed by both left and right eyes with parallax, the observer feels that the signal component having a position on images which does not change is located on the plane. On the other hand, the noise component having a position on images which changes with time is not present on the same plane as that of the signal, but is dispersed in a direction perpendicular to the image formed by the signal or imaged at a spatial position different from the image face formed by the signal. It is thus possible to surely remove noises from the image formed by the signal.

DESCRIPTION OF THE PREFERRED EMBODIMENTS

An embodiment of the present invention will hereafter be described by referring to drawings.

Figure 1:
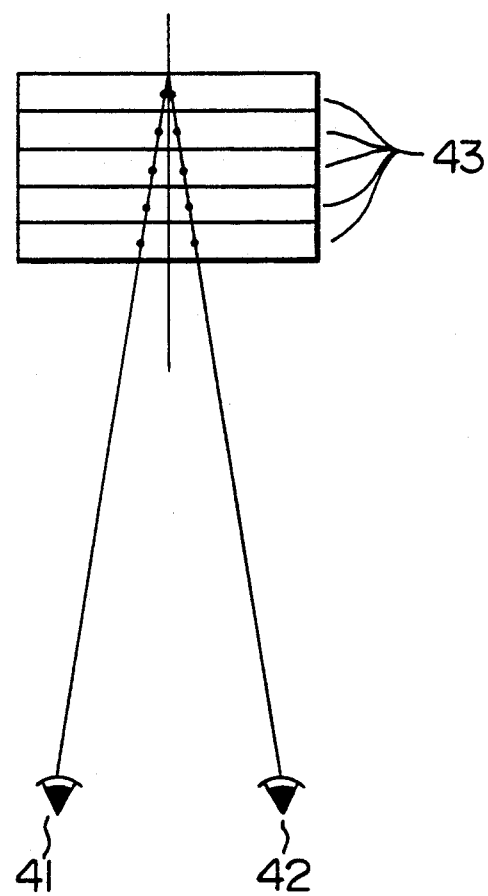
FIG. 1 shows a conventional method for constructing a stereoscopic image.
Figure 2:
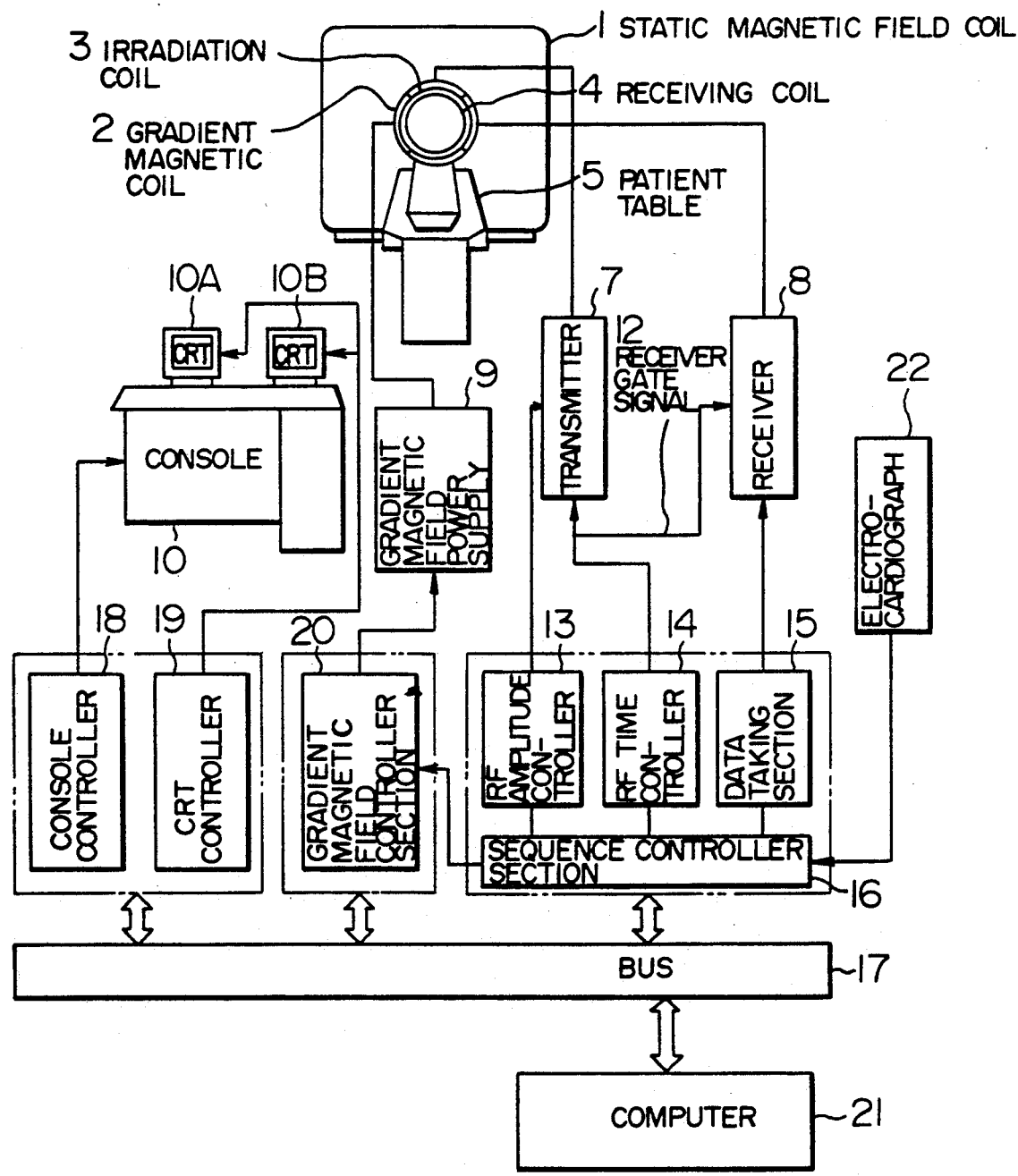
FIG. 2 is a block diagram of an MRI apparatus whereto an image noise reduction apparatus according to the present invention is applied.

FIG. 2 shows the system configuration of an MRI apparatus in which an image noise reduction apparatus of the present invention is incorporated. A static magnetic field coil 1 forms a principal part of the present system. Static magnetic field coils can be classified into superconductive type, normalconductive type and permanent magnet type. The case of static magnetic field coil of superconductive type is illustrated. The magnetic field strength is 0.5 T, and the bore diameter is 1 m. The degree of uniformity of the magnetic field is 5 ppm/30 cm dsv (sphere). A subject lies on a patient table 5 and is sent into the central part of the static magnetic field coil 1. A gradient magnetic field for acquiring spatial position information is superposed on a static magnetic field formed by the static magnetic field coil 1. A high frequency (RF) for generating the nuclear magnetic resonance phenomenon (NMR) is transmitted from a transmitter 7 to an irradiation coil 3. An NMR signal generated by the subject or materials to be inspected is sensed by a receiving coil 4 and transmitted to a receiver 8. In the NMR phenomenon, the phase information of the NMR signal is also important. Via a receiver gate signal 12, therefore, phases of the transmitter and the receiver are accurately synchronized.

Gradient magnetic field power supply 9 comprises power supply of three channels in order to independently generate gradient magnetic fields in three axis directions, i.e., X, Y and Z. Since the gradient magnetic field is applied in a pulsive form from a gradient magnetic field coil 2, high-speed response is requested. Generation of pulses is controlled by a gradient magnetic field controller section 20.

Manipulation of the system is performed by using a console 10. In addition to various keys, two CRTs 10A and 10B are equipped on the console 10. Among them, the CRT 10A is used for setting various parameters in an interactive form or operating the overall system, whereas CRT 10B is used for displaying obtained images.

Control over the entire system and high-speed arithmetic operation for image construction are conducted by a computer 21. Exchange of information between the computer 21 and each control system is performed via a bus 17. Control of various pulse sequences is exercised by a sequence controller section 16. A principal sequence relates to a combination of a high-frequency pulse and a gradient magnetic field.

With reference to FIG. 2, numeral 13 denotes an RF amplitude controller section, 14 an RF time controller section, 15 a data taking section, 18 a console controller section, 19 a CRT controller section, and 22 an electrocardiograph.

Further, in the present embodiment, the static magnetic field coil 1, the transmitter 7, the receiver 8 and so on constitute imaging means, whereas the CRT 10A, 10B, the computer 21 and so on constitute display means.

The basis of the imaging method using the NMR phenomenon will now be described by referring to FIGS. 3 and 4.

Figure 3:
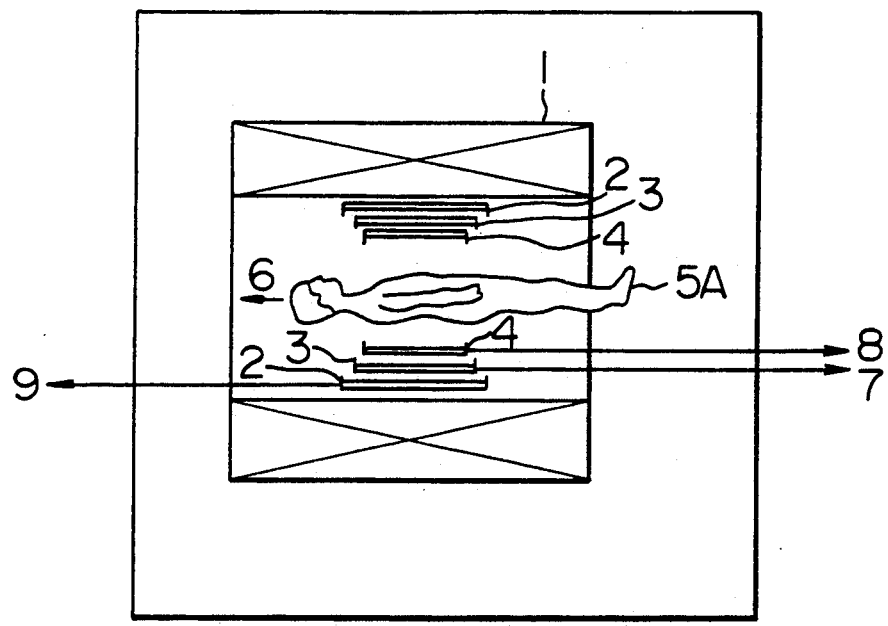
FIG. 3 is a detailed sectional view of a static magnetic field coil section.

A sectional view of a measurement section of the NMR imaging apparatus is shown in FIG. 3. A superconductive magnet comprises the static magnetic field coil 1 cooled to the liquid helium temperature having the gradient magnetic field coil 2, the irradiation coil 3 and the receiving coil inside thereof. The gradient magnetic field coil 2, the irradiation coil 3 and the receiving coil 4 are connected to the gradient magnetic field power supply 9, the transmitter 7 and the receiver 8, respectively. Further, the direction of the static magnetic field is indicated by an arrow 6. The direction of the static magnetic field is defined as the Z axis. As for the gradient magnetic field coil 2, gradient magnetic fields which are completely independent each other must be applied in three directions of X, Y and Z axes. Three kinds of coils are thus provided for the X axis, Y axis and Z axis, respectively. In FIG. 3, 5A denotes a subject.

Figure 4:
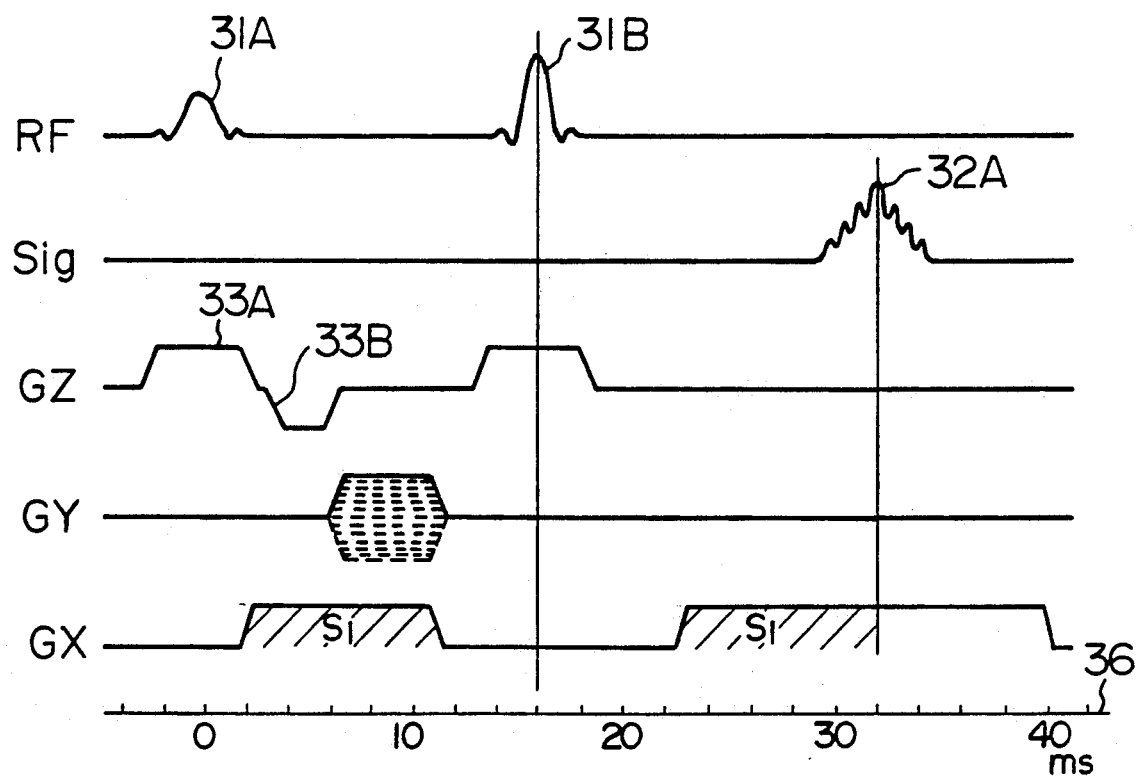
FIG. 4 shows pulse sequences for acquiring images.

FIG. 4 shows an example of pulse sequences, in which 31A and 31B denote pulse waveforms of high-frequency power irradiated from the irradiation coil 3 onto the subject 5A, and 32A denotes a signal obtained by amplifying an electromotive force existing in the receiving coil. Further, gradient magnetic field $G_Z$ is a gradient magnetic field of the Z direction applied in the direction of the static magnetic field. Gradient magnetic field $G_Y$ encodes the phase in the Y-axis direction. Gradient magnetic field $G_X$ functions to associate a coordinate in the X-axis direction with a frequency in a one-to-one manner. Since the gradient magnetic field $G_Y$ is typically used for generation of spin echo and hence often interpreted as a gradient magnetic field for readout. Numeral 36 denotes a time axis for clarifying the relationship between each of the above described pulse sequences and time.

Roles of the above described various pulses will now be described in more detail, and the principle of an image construction method referred to as two-dimensional Fourier method will be described.

In the example shown in FIG. 4, the sinc function is used for the waveform of the high-frequency pulse RF. Fourier transform of the sinc function is a rectangular wave. That is to say, the sinc function in time domain becomes a rectangular wave in the frequency domain, and hence it has only frequencies belonging to a certain limited section. With reference to FIG. 4, a gradient magnetic field pulse 33A is applied concurrently with the 90-degree pulse (i.e., a pulse for throwing down the nuclear spin by 90 degrees). Since the resonance condition in the NMR phenomenon is expressed by the following equation, only a specific tomographic plane in the Z-axis direction is selectively excited.

$$\omega_o = \gamma[H_o + H_G(Z)] \tag{1}$$

In the equation (1), $\omega_o$ is two angular velocity at a resonance point, $\gamma$ gyromagnetic ratio, $H_o$ magnetic flux density of the static magnetic field, and $H_G(Z)$ magnetic flux density of gradient magnetic field at position Z.

In typical NMR imaging, the frequency of selective irradiation is set in the range of thickness of the tomographic plane of 1 to 20 mm. In FIG. 4, the 180-degree pulse 31B is applied after the 90-degree pulse to obtain the spin echo signal 32A. (In the original two-dimensional Fourier method, the spin echo is generated by the gradient magnetic field and the 180-degree pulse is not used.)

The spin echo technique is a technique for realigning, after a predetermined time, the phase rapidly dispersed with an apparent lateral relaxation time $T_2^*$ by a nonuniform magnetic field. The mark * represents an apparent value. The gradient magnetic field is a kind of nonuniform magnetic field. For obtained a signal aligned in phase, it is necessary to invert the gradient magnetic field or apply the 180-degree pulse concurrently with the gradient magnetic field. When the gradient magnetic field is actually raised, each of the rise time and the fall time is finite and approximately 1 ms. In this transition interval, therefore, the phase is disturbed. In order to compensate this, a compensating pulse 33B is applied after the gradient magnetic field pulse 33A. The rise time and the fall time are canceled. Appearance equivalent to the case where a complete rectangular wave is applied is thus obtained.

Phase encode will now be described.

As the basic properties of behavior of nuclear spin in the NMR phenomenon, ① direction of magnetic moment, ② magnitude of magnetic moment, ③ the number of magnetic moments, ④ peturbation frequency of magnetic moment, and ⑤ phase of peturbation of magnetic moment can be mentioned. As the statistical result of these individual parameters, macroscopic behavior of magnetization can be described. In particular, frequency and phase are independent parameters. By encoding the phase, association with spatial coordinates can be obtained.

The phase is encoded by the gradient magnetic field $G_Y$. Since the quantity of phase encode depends upon the integral value of the gradient magnetic field pulse for encoding, it can be changed by changing the pulse amplitude or pulse width. In FIG. 4, the amplitude is changed.

If the gradient magnetic field $G_X$ in the X-axis direction is applied to spin so excited the 90-degree pulse 31A as shown in FIG. 4 as to perform coherent precession, the frequency of the precession changes linearly with respect to the X-axis direction. By applying the gradient magnetic field $G_X$ of the same polarity as the 180-degree pulse 31B after the pulse 31A, the rotation phase of the spin can be converged, and the spin echo signal 32A can be generated. Integral value S of the gradient magnetic field $G_X$ before the 180° pulse 31B is equivalent to that after the 180° pulse. Since they act on the spin in opposite directions, its influence upon the phase of the spin becomes zero. The X coordinate is in linear relation to the resonance frequency. By applying Fourier transform to the spin echo signal 32A, therefore, the relation of the signal strength to X coordinate can be obtained.

By applying Fourier transform to the Fourier transformed result above mentioned again with respect to the phase encode direction (i.e., Y-axis direction), the relation of signal strength to the Y-coordinate is obtained. Signal distribution on the X-Y plane is thus obtained. By displaying the signal strength on the CRT, therefore, the tomogram is obtained.

In accordance with the present invention, an identical region is imaged at changed times, and images obtained by seeing a part to be observed from an identical visual point are reconstructed from measurement signals obtained in each imaging. Further, two sheets of images taken at different times are juxtaposed as shown in FIG. 5.

For each of an image 51 for the left eye and an image 52 for the right eye, random noise 53 and strip noise 54 are present. Importantly, incoherent noise having no periodicity with respect to time is present in different positions respectively of two sheets of images. Even in case of coherent noise having periodicity with respect to time (i.e., signal taking-in), the probability that noises become the same phase is low if the imaging time is changed. Therefore, the coherent noise is also present in different positions respectively of two sheets of images.

Figure 5:
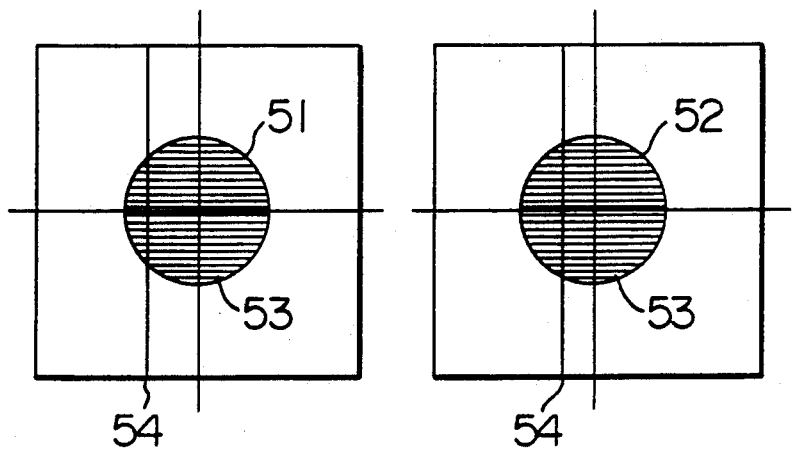
FIG. 5 shows arrangement of two sheets of images taken at different times.
Figure 6A:
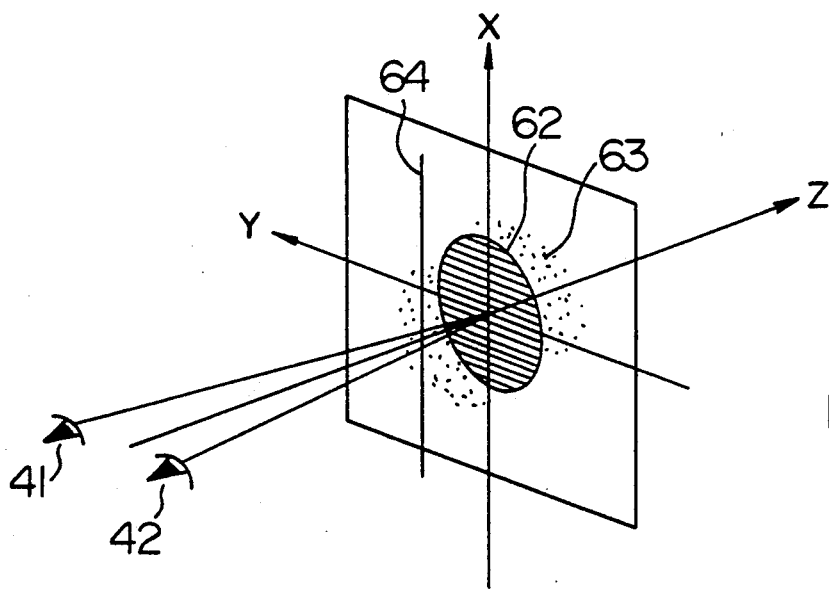
FIGS. 6A and 6B show how noises are reduced by the present invention.
Figure 6B:
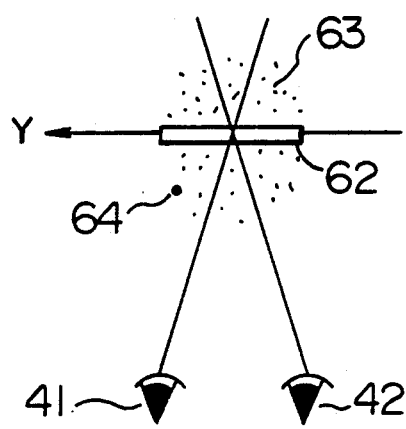

These two sheets of images are set apart on an identical plane side by side as shown in FIG. 5 and observed by both eyes or by using stereo glass. A pseudostereoscopic image as shown in FIG. 6A is thus obtained. FIG. 6B is a top view for illustrating how the brain feels the image steroscopically. That is to say, the left image is the same as the right image with respect to the signal component. Even if stereoscopic vision is effected by using both eyes, therefore, only one synthesized image 62 resulting from complete superposition on the same plane is observed. As for the noise component, however, it is separated by the stereoscopic vision from the image formed by the signal component and it is dispersed in a direction perpendicular to the image plane. The incoherent noise component is dispersed on an average in three dimensions and observed as synthetic random noise 63. Further, the coherent noise component forms a certain shape in three-dimensional space, but it is observed as synthetic strip noise 64 in a position located apart from the plane formed by the signal. Since the signal component is equivalent to that of two sheets of images superposed each other, it is increased to twice. Since the noise component is random, its average strength is statistically increased to $\sqrt{2}$ times. Therefore, the image is observed with the signal-to-noise ratio improved to at least $\sqrt{2}$ times. The quantity of improvement in the signal-to-noise ratio resulting from dispersion of the noise component in three-dimensional directions can not be easily estimated because the human sense directly relates thereto. If noise having a frequency different from the signal read-in frequency is present, for example, however, noise of a difference frequency appears as beat noise. In case of two sheets of images having beat noise mixed in different positions, the line formed by beat is observed as if it is lifted out of the image surface formed by the signal. As a result, the line formed by the beat can be definitely distinguished from the signal.

By providing a display device for displaying two sheets of images as shown in FIG. 5 on a display screen side by side and a stereo glass device so installed as to match with the display device as an apparatus whereto the image noise reduction method according to the present invention is applied, an image with noise reduced can be easily observed.

The present invention is applicable to not only MRI apparatuses but also X-ray CT apparatuses, ultrasonic diagnostic apparatuses and other apparatuses which construct images and display them as the result of measurements.

We claim:

1. An image noise reduction method comprising the steps of:
    a) taking a first measurement to obtain an image signal from a subject;
    b) taking a second measurement to obtain an image signal of the same kind as that of said image signal from said subject;
    c) deriving a first image having at least one sheet for an identical region and an identical visual point from the image signal obtained by said first measurement;
    d) deriving a second image having at least one sheet for said identical region and said identical visual point from the image signal obtained by said second measurement;
    e) displaying said first image and said second image on an identical plane side by side; and
    f) observing said first image and said second image with parallax changed, whereby the effective signal component of said images is focused on said plane whereas the noise component is dispersed in a direction perpendicular to said plane, resulting in an improved signal-to-noise ratio of said images when observed.

2. An image noise reduction method according to claim 1, wherein each of said first measurement and said second measurement comprises the steps of applying a high-frequency pulse and a gradient magnetic field to said subject in an MRI apparatus and measuring a magnetic resonance signal supplied from said subject.

3. An image noise reduction apparatus comprising:
    a) means for measuring an image signal supplied from a subject at different times at least twice;
    b) means responsive to each of said measurements for reconstructing an image for an identical region and an identical visual point from said image signal obtained by said measurement;
    c) means for displaying the images obtained respectively from said measurements on an identical plane side by side so as to form two sheets; and
    d) means responsive to observation of said two sheets of images arranged side by side simultaneously with both eyes for matching the parallax in observing said two sheets of images with the parallax of said both eyes, whereby the effective signal component of said images is focused on said plane whereas the noise component is dispersed in a direction perpendicular to said plane, resulting in an improved signal-to-noise ratio of said images when observed.

4. An image noise reduction apparatus according to claim 3, wherein said parallax matching means comprises a stereo glass device.

5. An image noise reduction apparatus according to claim 3, wherein said measuring means is an MRI device including means for applying a high-frequency pulse and a gradient magnetic field to said subject and measuring a magnetic resonance signal supplied from said subject.

* * * * *